United States Patent [19]
Laptewicz, Jr. et al.

[11] Patent Number: 5,984,957
[45] Date of Patent: Nov. 16, 1999

[54] RADIALLY EXPANDED PROSTHESES WITH AXIAL DIAMETER CONTROL

[75] Inventors: Joseph E. Laptewicz, Jr., Wayzata, Minn.; Thomas A. Silvestrini, Alamo, Calif.

[73] Assignee: Schneider (USA) Inc, Plymouth, Minn.

[21] Appl. No.: 09/079,806

[22] Filed: May 15, 1998

Related U.S. Application Data

[60] Provisional application No. 60/055,238, Aug. 12, 1997.

[51] Int. Cl.$^6$ ............... A61F 2/06; A61F 2/02; A61F 2/04; A61M 29/00
[52] U.S. Cl. ............... 623/1; 623/11; 623/12; 606/191; 606/194
[58] Field of Search ............... 623/1, 11, 12, 623/66, 900; 606/191, 194; 604/104; 600/36

[56] References Cited

U.S. PATENT DOCUMENTS

| | | | |
|---|---|---|---|
| 5,507,767 | 4/1996 | Maeda et al. | 606/198 |
| 5,800,456 | 9/1998 | Maeda et al. | 606/198 |
| 5,817,126 | 10/1998 | Imran | 606/198 |
| 5,824,043 | 10/1998 | Cottone, Jr. | 623/1 |
| 5,824,053 | 10/1998 | Khosravi et al. | 623/1 |
| 5,824,054 | 10/1998 | Khosravi et al. | 623/1 |
| 5,824,056 | 10/1998 | Rosenberg | 623/1 |
| 5,888,201 | 3/1999 | Stinson et al. | 623/1 |
| 5,891,191 | 4/1999 | Stinson | 623/1 |

*Primary Examiner*—Mickey Yu
*Assistant Examiner*—Dinh X. Nguyen
*Attorney, Agent, or Firm*—Frederick W. Niebuhr

[57] ABSTRACT

A tubular, radially self-expanding stent includes a latticework of interbraided, helically wound resilient structural strands. An axial control member is secured to the tubular latticework at axially spaced apart proximal and distal coupling locations. At the proximal location, the control member is coupled slidably, to permit an adjustment of the axial distance between the coupling locations, thus to selectively adjust the radius profile of the latticework between the two locations. To set a desired radius profile, the control member either is crimped near the proximal location or fixed within a self-locking connector. The control members, preferably monofilament strands, can be elastic or substantially inextensible. Two or more control members can be used if desired. In an alternative embodiment, recovery metal control members are fixed at their opposite ends to the latticework, then plastically deformed by elongation to axially elongate and radially reduce the latticework. Following deployment, the control members are heated sufficiently to cause the control members to return to their shorter, nominal shapes, to axially shorten and radially enlarge the stent. Both versions preferably feature selvaged ends.

42 Claims, 4 Drawing Sheets

RADIALLY EXPANDED PROSTHESES WITH AXIAL DIAMETER CONTROL

This application claims the benefit of priority of Provisional Application No. 60/055,238 entitled "Wire Braided Tube Containing Axial Members of Triaxial Braid to Control Diameter of Vascular Stent," filed Aug. 12, 1997.

BACKGROUND OF THE INVENTION

The present invention relates to tubular prostheses such as stents insertable into blood vessels and other body lumens, and more particularly to features in such prostheses for controlling the amount or nature of their radial expansion.

A variety of treatment and diagnostic procedures involves devices intraluminally implanted into the body of a patient. Among these devices are stents, such as disclosed in U.S. Pat. No. 4,655,771 (Wallsten). The Wallsten devices are tubular, braided structures formed of helically wound thread elements. The stents are deployed using a delivery catheter such as disclosed in U.S. Pat. No. 5,027,377 (Burton, et al.). With the stent positioned at the intended treatment site, an outer tube of the delivery catheter is withdrawn, allowing the stent to radially expand into a substantially conforming surface contact with a blood vessel wall or other lumen-defining tissue.

An alternative stent construction features plastically deformable metallic strands, which also can be helically wound. Such stent does not require an outer tube or other feature to maintain it in a reduced-radius state during delivery. Radial expansion at the treatment site requires a dilatation balloon or other external expansion means.

Regardless of whether stents are self-expanding or plastically deformable, they characteristically have an open mesh or open frame construction, or otherwise are formed with multiple openings to facilitate radial enlargements and reductions, and to allow tissue ingrowth. Such stents typically expand axially or longitudinally as they radially contract, and conversely expand radially as they are axially shortened.

Self-expanding stents frequently are favored, not only because they do not require a balloon or other external expansion device, but also because of the radially outward residual force exerted against the surrounding tissue by a properly sized stent once deployed. A variety of constructions are available, ranging from a single coil (e.g., of a memory metal such as Nitinol) to multiple monofilaments (metalic or polymeric) arranged in sets of oppositely directed helices.

While the advantages of self-expanding stents are widely known, it would be beneficial to provide more positive control over the extent of a stent's radial expansion, once it is released from within a deployment device. Self-expanding stents characteristically have a relaxed (free of external stress) state toward which they expand when released. After delivery and release of a stent at a selected treatment site, it may appear that the relaxed state radius is less than that desired for the application. Corrective action, such as retrieving the stent and replacing it with a larger-diameter device, might be required.

Even in situations where the deployed device is considered satisfactory, it might be desired to increase or decrease, in situ, the amount of radial residual force which the device exerts against surrounding tissue. Conventional stent constructions do not afford this option.

Another consideration arises if unexpected irregularities in vasculature are encountered at the treatment site. While stents can be configured to have diameter gradients or irregular profiles, this capability does not address the desire to reconfigure a stent toward conformity with an unanticipated tissue irregularity at the treatment site.

Implanted devices are subject to vessel constriction or closure if their radially outward acting restoring force is overcome by tissue contractions.

Therefore, it is an object of the present invention to provide a body insertable prosthesis including a control feature for determining the amount of radial expansion of the prosthesis upon its release from a deployment device.

Another object is to provide a means for controllably varying the amount of radially acting restoring force in a self-expanding stent radially enlarged to a given diameter.

A further object is to provide a tubular self-expanding prosthesis radially expandable over a selected portion of its length, either to the exclusion of or to a greater degree than a remaining portion of the device length.

Yet another object is to provide a body insertable self-expanding tubular prosthesis usable in body lumens having a wider range of diameters.

SUMMARY OF THE INVENTION

To achieve these and other objects, there is provided a body insertable prosthesis. The prosthesis includes a body compatible and generally tubular prosthesis structure. The structure is enlargeable radially by an axial shortening thereof, and alternatively reducible radially by its axial elongation. At least one elongate control member is coupled to the prosthesis structure at a first coupling location. The control member further is joined to the prosthesis structure at a second coupling location, spaced apart axially from the first location in a manner that allows the control member to travel axially relative to the prosthesis structure, while remaining substantially axially fixed relative to the prosthesis structure at the first coupling location. As a result, an axial spacing between the first and second coupling locations is adjustable toward a selected amount corresponding to a selected radius profile over a region of the prosthesis structure between the coupling locations.

The radius profile, i.e. the variance or gradient (if any) in the radius of the prosthesis over the region between coupling locations, depends on the relaxed-state profile of the prosthesis as well as the axial spacing between the coupling locations. For example, a taper in the prosthesis generally is maintained as the coupling locations are brought closer together. In the case of a tubular prosthesis having the same radius over its complete length, the selected radius profile, typically, also exhibits a uniform radius over the region between the coupling locations.

Preferably the control member is slidengly coupled to the prosthesis structure through a connector that is fixed to the prosthesis structure and receives the control member slidably. A preferred control member is a monofilament or strand extending axially along the prosthesis structure. The connector can be configured to have a tight, frictional hold on the strand, which tends to fix the strand with respect to the structure after the strand has been moved, typically pulled, to its desired axial position within the connector. Alternatively, an annular clamp or locking mechanism can be mounted slidably along the strand, for locking the strand into place.

The strand can be constructed of metal or a suitable polymer. The strand can be resilient, or substantially inextensible. A resilient strand adds to the elastic restoring force exerted radially outwardly by a self-expanding stent surrounded by and compressed by vascular tissue. Specifically, the strand resists axial elongation of the prosthesis along the region between the first and second coupling locations.

The coupling locations can be at the opposite ends of the prosthesis structure. For certain uses, one of the coupling locations is advantageously positioned along a medial region of the prosthesis structure. For example, forming the first coupling location at a distal end of the stent while forming the second coupling location at about the midpoint of the stent, enables a controlled radial expansion of the distal half of the stent with a negligible effect on the proximal half of the stent.

One preferred stent construction employs a plurality of monofilament metal or polymeric strands, interbraided in at least two sets of oppositely directed helices. These structures frequently have exposed wire ends. Thus, according to another aspect of the present invention, there is provided a braided prosthesis structure including a plurality of structural strands, intermingled with one another to form a generally tubular prosthesis structure. The structure is enlargeable radially by an axial shortening, and alternatively reducible radially by an axial elongation. The structure has two opposite open ends. A plurality of connectors are secured integrally to the strands at at least one of the open ends, to selvage at least one open end. When a strand is fixed to the prosthesis structure to control radial expansion as discussed above, at least one of the connectors can be configured to slidably accept the strand, and further may be adapted to lock the strand into place once the appropriate axial position is determined.

Yet another aspect of the present invention is a body insertable and controllably expandable prosthesis. The prosthesis includes a body compatible, generally tubular prosthesis structure. The structure is enlargeable radially by an axial shortening, and alternatively is reducible radially by an axial elongation. The prosthesis further includes at least one control member. The control member is constructed of a recovery metal, with a nominal shape defining a nominal length between opposite first and second ends of the control member. The control member is plastically deformable to an altered shape defining an altered length between the opposite ends that is different than the nominal length. The control member tends to return to the nominal shape from the altered shape responsive to a predetermined change in temperature. The control member, proximate its first and second ends, is joined integrally with respect to the prosthesis at first and second axially spaced apart locations. Accordingly, when the prosthesis and the plastically deformed control member are subjected to the temperature change, an axial distance between the first and second locations is selectively altered, thus selectively adjusting a radius profile of the prosthesis structure between the first and second locations.

In one preferred prosthesis, several control members are attached to the prosthesis in an array of axially directed, circumferentially spaced apart members. Each control member resembles a sinusoidal curve in its nominal shape, and when plastically deformed is linear. Accordingly, plastically deforming the members axially elongates the prosthesis, reducing its radius as well. When the prosthesis is subjected to the predetermined temperature change, more particularly heated to a temperature at or above a characteristic threshold of the recovery metal involved, the control members return to the nominal shape in concert, axially contracting and radially enlarging the prosthesis.

Thus, in accordance with the present invention, one or more axial members are coupled to a tubular prosthesis structure to control the degree of radial expansion and axial contraction of the structure. The control members can be inextensible to positively control expansion, or resilient to augment the elastic restoring force exerted by the helical windings or other non-axial elements of the structure. The control elements can be connected at predetermined locations, including medial locations along the prosthesis, to enable selective radial adjustments including tapers or gradients, and other irregular features. Along with determining radial expansion, the axial members add to the ability of the prosthesis to resist closure or constriction caused by contractions of tissue around the treatment site.

IN THE DRAWINGS

For a further understanding of the above and other features and advantages, reference is made to the following detailed description and to the drawings, in which.

DETAILED DESCRIPTION OF THE PREFERRED EMBODIMENTS

Figure 1:
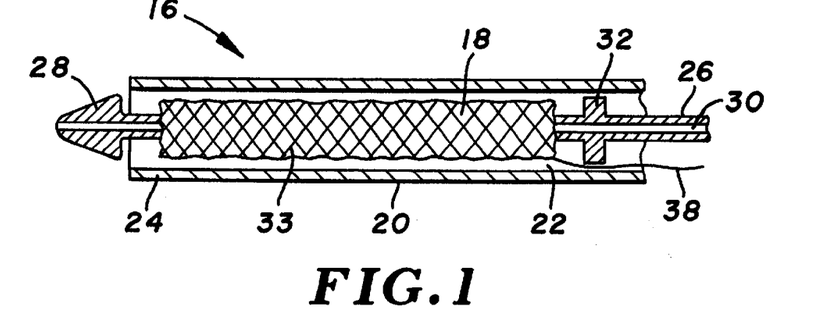
FIG. 1 is a side elevation, partially in section, showing a stent constructed in accordance with the present invention contained within a deployment device.

Turning now to the drawings, there is shown in FIG. 1 a deployment device 16 for delivering a stent 18 to an intended fixation site or treatment site within a body lumen, then controllably releasing the stent for radial self-expansion and fixation within the body lumen.

The deployment device includes an elongate and flexible outer catheter 20 constructed of a bio-compatible polymer such as polyurethane. A central lumen 22 runs the length of catheter 20. A distal end region 24 of the outer catheter surrounds stent 18. An inner catheter 26 is contained within lumen 22 and runs along the entire length of the outer catheter. At the distal end of inner catheter 26 is a tapered distal tip 28 which extends beyond the outer catheter. Stent 18 surrounds inner catheter 26, confined between the inner and outer catheters. A lumen 30 through the inner catheter accommodates a flexible guide wire tracked by device 16 as it is advanced intra-lumenally toward the treatment site.

Stent 18 is formed of resilient materials, and is shown elastically compressed into a radially-reduced and axially-elongated delivery state. Outer catheter 20 maintains the stent in the delivery state against its elastic restoring force. An annular detent 32, mounted to inner catheter 26, occupies a space between the inner and outer catheters to limit proximal travel of the stent relative to the inner catheter. Accordingly, when the outer catheter is moved proximally relative to the inner catheter, detent 32 prevents stent 18 from following the outer catheter.

Catheters 20 and 26, while maintaining the stent in the delivery state, are moved translumenally to deliver the stent to the fixation site. Once the stent is located as intended, inner catheter 26 is held stationary while outer catheter 20 is withdrawn proximally. Detent 32 maintains the stent properly aligned as the stent radially self-expands toward an intimate contact with tissue at the fixation site. Preferably the stent does not expand completely to its relaxed state (i.e., its condition when not subject to any external force). Consequently, the stent exerts a residual force radially outwardly on surrounding tissue, which tends to acutely fix the prostheses. At this point, the stent has a diameter larger than the diameter of distal tip 28, so that the inner catheter and tip can be proximally withdrawn to leave the stent in place.

Figure 2:
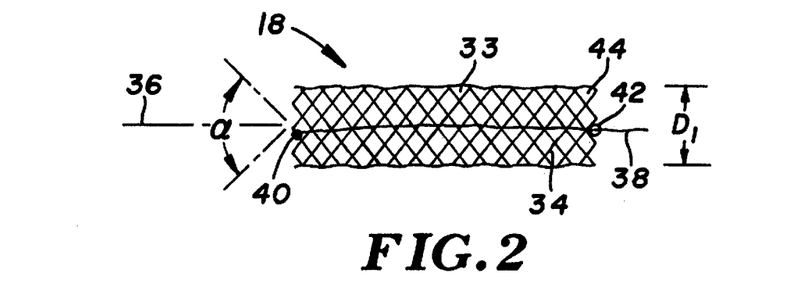
FIG. 2 shows the stent in side elevation in an unconstrained, radially expanded state.

In FIG. 2, stent 18 is shown in its nominal or relaxed state, indicating the absence of an external force. Stent 18 includes a framework or latticework 33 of resilient monofilament structural strands 34. The strands are arranged in two sets of parallel helices wound in opposite directions about a common longitudinal axis 36. The strands intersect one another to define a braid angle alpha ($\alpha$) bisected by the longitudinal axis. The braid angle is in the range of about 60–150°, more preferably about 90–140°.

The braid angle is defined with reference to the relaxed state of the latticework. Compression of the stent into the delivery state substantially reduces the braid angle. At the same time, the braid angle influences the relationship between radial compression and axial elongation of the stent. Smaller braid angles result in less axial shortening for a given amount of radial enlargement. Conversely, with a larger braid angle, the same radial expansion results in more axial shortening. For a given strand size and strength, a larger braid angle imparts greater resistance to radial compression and more positive acute fixation.

Structural strands 34 are elastic, strong, biocompatible, hemocompatible, and resistant to corrosion and fatigue. Suitable materials include certain stainless spring steels, cobalt-based alloys, titanium alloys, and clad composites as disclosed in U.S. Pat. No. 5,628,787. Several preferred cobalt-based alloys are sold under the brand names Elgiloy, Phynox, and MP35N. The strands also can be formed of polymers, including PET, polypropylene, PEEK, high density polyethylene, polysulfone, acetyl, PTFE, FEP, and polyurethane. Suitable strand diameters are about 0.002–0.015 inches.

Stent 18 also includes a control filament 38, coupled to the latticework at the proximal and distal ends of the latticework and extending proximally beyond the latticework. Control filament 38, preferably of monofilament construction, can be formed of the same materials used to form the latticework. Further, in certain applications it may be desired to provide a control filament having a modulus of elasticity much higher than the elastic modulus of the latticework material, even to the point that the control filament is considered inextensible rather than resilient. Thus, control filament materials can range beyond those suitable for the structural strands, although both must be strong, biocompatible, hemocompatible, and resistant to corrosion and fatigue.

Control filament 38 is coupled to the latticework at two points spaced apart axially from one another: a distal end coupling 40 and a proximal end coupling 42. The distal end coupling is fixed, i.e., the distal end of the control filament is integral with the distal end of the latticework. When the structural strands and control strand are formed of the same type of material, distal coupling 40 is conveniently formed by thermal bonding. Specifically, the thermal bond is a weld as shown in FIG. 2 for metal strands. Alternatively, a fusion bond can be formed when all of the strands are polymeric.

Proximal end coupling 42 accommodates axial movement of the control filament relative to the latticework. As shown in FIG. 2, proximal coupling 42 is a loop formed in one of the structural strands, with the control strand extending through the loop. By moving the latticework proximal end 44 along control filament 38, the user changes the axial distance between the two coupling locations, thus also changing the latticework radius over its length between the coupling points, which in this case encompasses the full length of the latticework.

Figure 3:
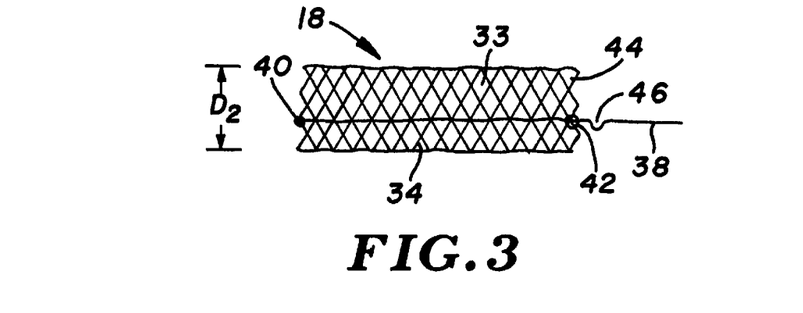
FIG. 3 shows the stent in side elevation, further radially expanded through use of an axial control filament.

As best seen in FIG. 3, stent 18 further incorporates a control feature that allows the user to set the axial position of control filament 38 relative to latticework 33. More particularly, this feature is a crimp 46 formed along the metal control filament proximally of loop 43. The crimp is formed after stent 18 is placed at the fixation site and allowed to radially expand into contact with surrounding tissue, and further after at least a slight additional axial shortening/radial expansion of the stent, so that the latticework bears against crimp 46 and maintains control filament 38 in tension. The additional axial shortening increases the amount of tensile force along control filament 38, in turn increasing the tendency in stent 18 to resist radial compression. In FIG. 3, control filament 38 provides a tensile force that maintains the latticework at a larger diameter $D_2$ than the relaxed-state diameter $D_1$ shown in FIG. 2.

Figure 4:
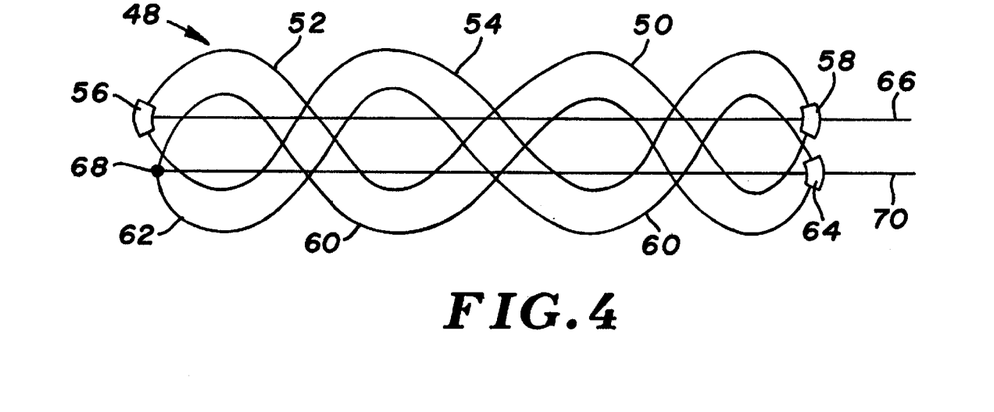
FIG. 4 shows an alternative embodiment stent including selvaging connectors for coupling an axial control filament.

FIG. 4 schematically illustrates an alternative stent 48 with a latticework 50 of interwoven helically wound structural strands. Although the latticework includes multiple strands, only a few of the strands are illustrated: a pair of strands 52 and 54 coupled to one another by a distal end connector 56 and a proximal end connector 58; and a substantially longer strand 60 having a distal end fold or loop 62, with its ends coupled by a proximal end connector 64. The connectors are located at the intersections of oppositely directed structural strands. Distal end connector 56 integrally couples the distal ends of structural strands 52 and 54, and the distal end of a control strand 66. A weld 68 integrally secures the distal end of a second control strand 70 to structural strand 60 along loop 62. While connector 56 and weld 68 are shown on the same device for convenience of illustration, a device typically would incorporate either one approach or the other. In either event, at the device distal end, the control strands are prevented from moving axially relative to the structural strands.

Figure 5:
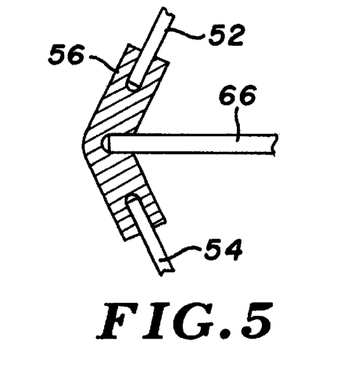
FIG. 5 is an enlarged view of one of the connectors.

As seen in FIG. 5, distal connector 56 has openings for receiving the distal ends of the strands, in each case providing a substantially tight fit for a frictional hold on the associated strand end. The tight fit can be achieved, for example, using a shrink-fit polymer. Alternatively, an adhesive can secure each strand end.

Figure 6:
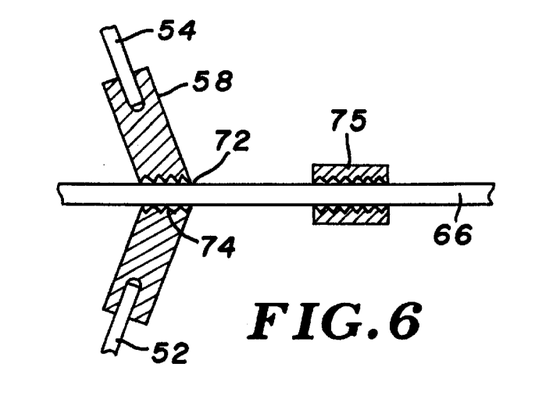
FIG. 6 is an enlarged view showing another one of the connectors in section.

As seen in FIG. 6, proximal end connector 58 has openings to receive the proximal ends of structural strands 52 and 54 in a tight or integral coupling as just described. In contrast, an axial opening 72 through the connector is sufficiently large to allow the connector to the slide along control strand 66. However, due to a row of annular serrations 74 along opening 72, control strand 66 does not slide freely, but only in response to the application of an external force. Accordingly, connector 58 incorporates a self-locking feature that facilitates setting a desired axial distance between the proximal and distal connectors, or between the proximal connector and a weld or other coupling, without the need for a crimp in the control strand. As an alternative, opening 72 can allow free sliding of the control strand, with a more tightly mounted locking sleeve 75 positionable to set the axial distance between connectors.

While two control strands are shown, stent 48 may be provided with multiple control strands distributed evenly about its circumference, or may require only a single control strand.

Connectors 56 and 58, in addition to securing the control strands, also selvage the proximal and distal ends of the latticework to eliminate what otherwise would be exposed ends of the metal structural strands. When just a few control strands are required, additional connectors can be provided solely for joining the free ends of structural strands.

Figure 7:
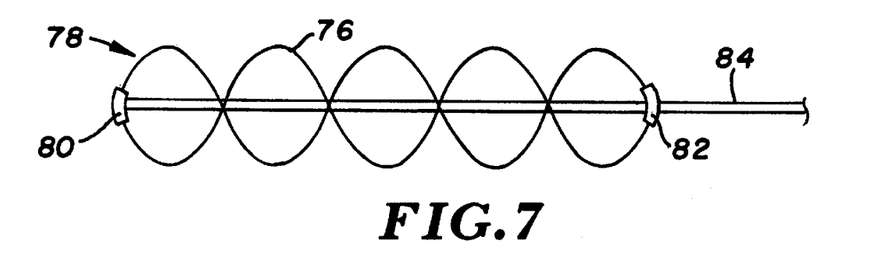
FIG. 7 is a schematic elevation of another alternative embodiment stent.

FIG. 7 schematically illustrates a pair of structural strands 76 of an alternative embodiment stent 78, coupled at their distal ends by a distal end connector 80, and at their proximal ends by a proximal connector 82. An axial control member 84 is integrally received within distal connector 80 and slides within proximal connector 82. As compared to control strands 66 and 70 of stent 48, the primary difference is that control member 84 is formed with a larger diameter than its counterparts, and thus is sufficiently stiff in the axial direction to axially elongate (and radially contract) stent 78 from its relaxed state, by a sliding of the proximal connector proximally along the control member.

Figure 8:
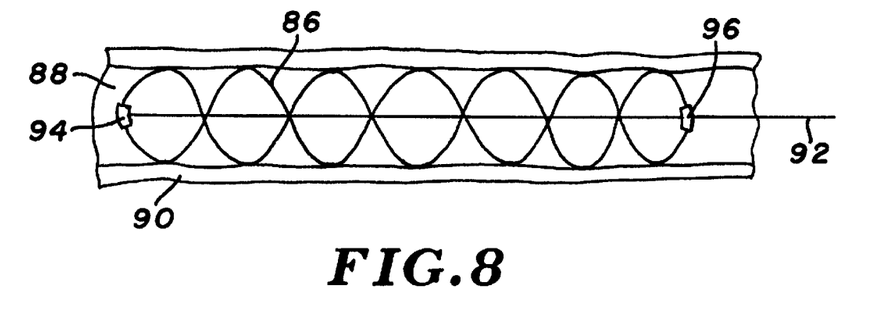
FIGS. 8 and 9 illustrate the deployment and shaping of the stent shown in FIG. 4.
Figure 9:
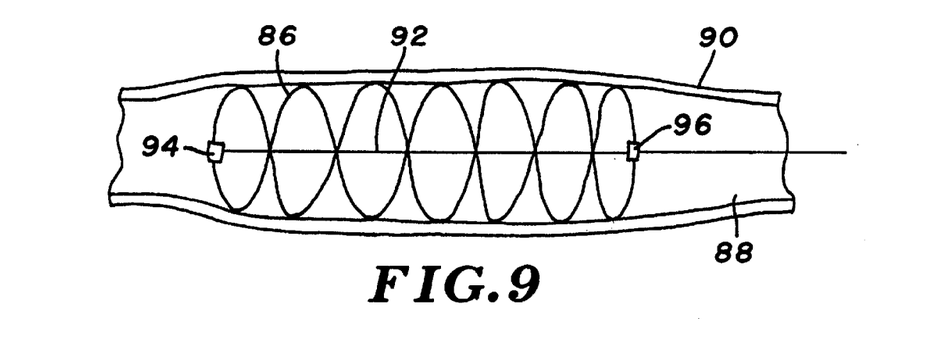

FIGS. 8 and 9 schematically illustrate, in part, the deployment of a stent 86 within a blood vessel 88 at a fixation location along a vessel wall 90. To the stage illustrated in FIG. 8, deployment proceeds in a manner that is known and not particularly germane to the present invention. More particularly, device 16 or another suitable device is advanced translumenally to an appropriate alignment near the fixation site, then manipulated to release stent 86, allowing its radial expansion into contact with tissue wall 90 as shown. An axially extending control filament 92 is coupled integrally at a distal coupling 94, and slides relative to the stent at a proximal coupling 96.

At this stage, a crimp can be formed in control filament 92 as in FIG. 3, or a self-locking connector as in FIG. 6 can be left in the position shown. As a result, a tensile force from the control filament augments the elastic restoring force in the coiled structural strands, to more effectively resist radial contraction of the vessel.

A further advantage of the invention is realized by locking the stent proximal end along the control strand as shown in FIG. 9, i.e. distally of the location shown in FIG. 8. This increases the stent's resistance to radial contraction, first by increasing tension along the control filament, and second by axially shortening and radially enlarging the latticework to increase the braid angle.

This latter feature is particularly beneficial in the event that the fixation site along vessel 88 is larger in diameter than anticipated, leading to deployment of a stent having less than the most preferred diameter. Under the circumstances, a stent without a control member, i.e. relying solely on the restoring force within the structural strands, may not provide a restoring force sufficient for acute fixation or resistance to contraction. Retrieval of the stent and deployment of a larger size stent may be required.

By contrast, stent 86 can be reliably secured and offer sufficient resistance to vessel constriction, even if the vessel size is larger than anticipated before deployment. In such case, the proximal end of stent 86 simply is moved distally to a greater degree than previously thought necessary and fixed by a crimp or a self-locking connector, further radially enlarging the stent to provide sufficient fixation and resistance to contraction.

Figure 10:
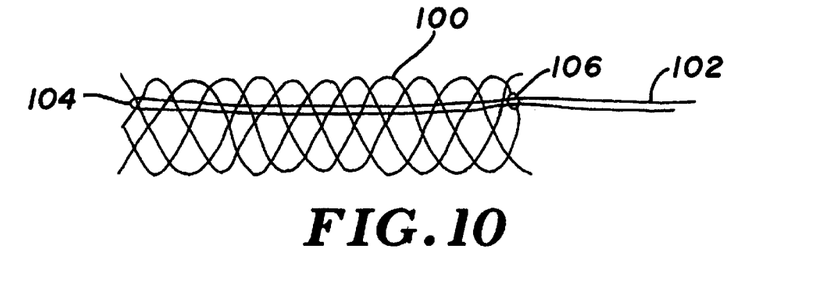
FIGS. 10 and 11 illustrate further alternative embodiment prostheses, incorporating dual filament axial controls.

FIG. 10 illustrates a further alternative embodiment stent 100 with interbraided helical structural strands, in which a control member 102 is formed from a single strand, folded or doubled over upon itself to form a looped end 104 for the distal coupling. The doubled strand is placed through a loop 106 at the proximal end of the latticework.

Figure 11:
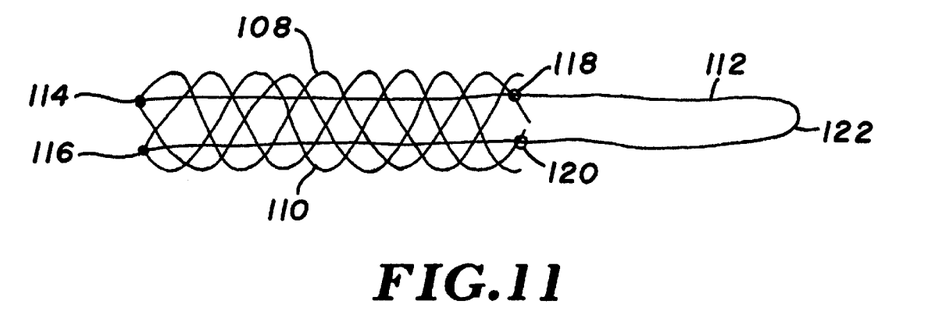

In FIG. 11, a further alternative stent 108 is formed of a latticework including oppositely directed interwoven helical structural strands 110. Stent 108 also incorporates a control member 112 that is doubled or looped as in FIG. 10. However, in this case free ends 114 and 116 of the doubled control member are welded or otherwise integrally secured to a distal end of the latticework, and the control member is retained slidably in proximal end loops or clamps at 118 and 120. The proximal, looped end 122 of the control member can be pulled while the proximal end of stent 108 is held stationary, to axially shorten and radially enlarge the stent.

Figure 12:
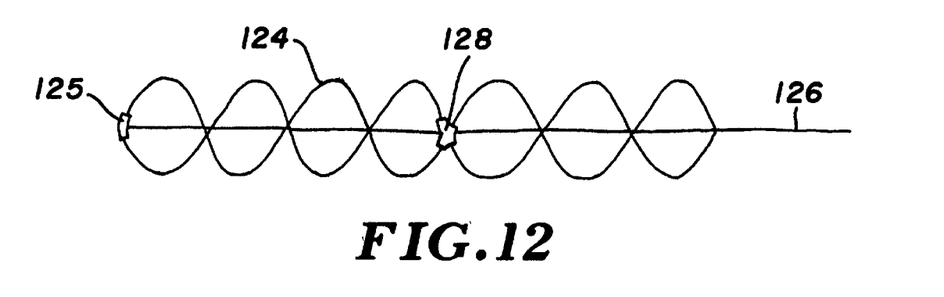
FIGS. 12 and 13 illustrate an alternative embodiment stent with a control filament coupled to selectively radially enlarge only a distal segment of the stent.
Figure 13:
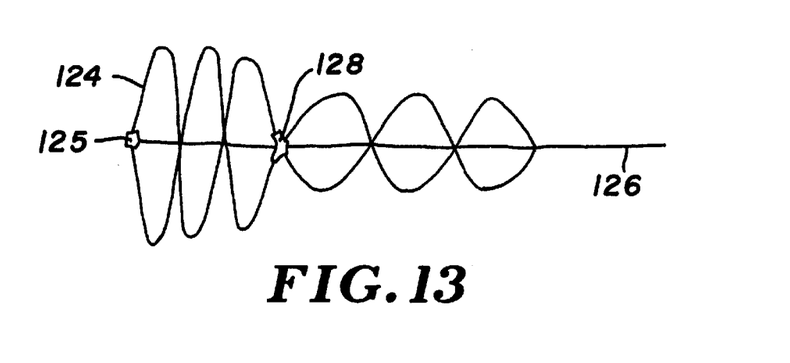

FIGS. 12 and 13 illustrate another alternative embodiment stent 124 formed by interbraided oppositely directed helical structural strands. A control strand 126 is integrally secured to the distal end of stent 124 by a connector 125. Further, control strand 126 is slidably coupled to the latticework through a connector 128 similar to connector 58 and FIG. 6, positioned medially along the stent rather than at its proximal end. In this arrangement, control strand 126 can be manipulated to selectively axially shorten and radially expand only a distal region of the stent, i.e. the region between connectors 125 and 128. FIG. 13 illustrates the result of selectively locking the control strand to provide a larger distal radius.

Figure 14:
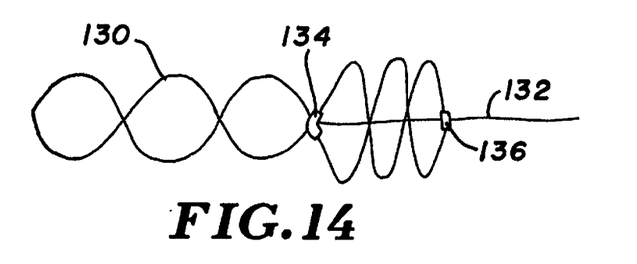
FIG. 14 illustrates another alternative embodiment stent incorporating a feature for radially enlarging only a proximal section.

FIG. 14 illustrates a stent 130 in which a control strand 132 is fixed at 134 along a medial region of the stent, and slidably secured at 136 to the proximal end of the stent, thus to selectively radially enlarge only a proximal region. In the case of stent 124 or stent 130, further control strands can be provided to enlarge further selected regions along the stent length, affording considerable flexibility in the stent's radius profile (i.e. the variance in stent radii over the stent length) to conform to body lumen irregularities.

Figure 15:
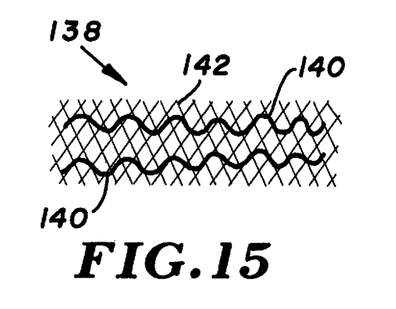
FIGS. 15 and 16 illustrate yet another alternative embodiment stent incorporating recovery metal control filaments.
Figure 16:
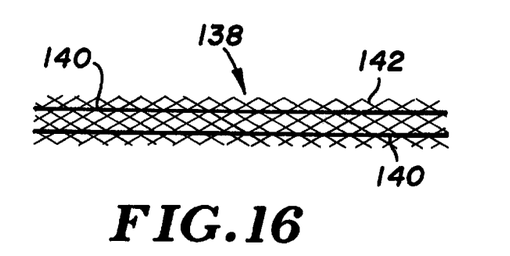

FIGS. 15 and 16 illustrate a further alternative embodiment stent 138 including a latticework of interbraided helical strands, and several control members 140 formed of a recovery metal, for example, a titanium-nickel alloy sold under the brand name "Nitinol." The recovery metal members are plastically deformable away from a nominal shape, so long as they remain below a predetermined threshold temperature. When heated to the threshold or above, the metal members assume the nominal shape.

In FIG. 15, control members 140 are shown in the nominal shape: a crimped, axially shortened, somewhat sinusoidal configuration. Each of the control members is integrally secured, at its proximal and distal ends, to the proximal and distal ends of latticework 142, respectively. Accordingly, the latticework axially expands and contracts along with the control members.

In FIG. 16, control members 140 are shown plastically deformed to an elongated, linear state, axially elongating and radially reducing the latticework to facilitate intraluminal delivery of the stent. Once deployed, control members 140 are heated at least to the threshold temperature, whereupon they return to the shortened state illustrated in FIG. 15, thus to axially shorten and radially enlarge the stent.

As compared to the previously discussed embodiments, this approach affords more control over the degree of radial expansion imparted by the control members. Radial enlargement is accomplished without physical manipulation of the stent, requiring only heating of the control members. This version, however, lacks the capability of adjusting the axial setting of the stent along the control member or members, to selectively vary the degree of radial enlargement.

Figures 17, 18:
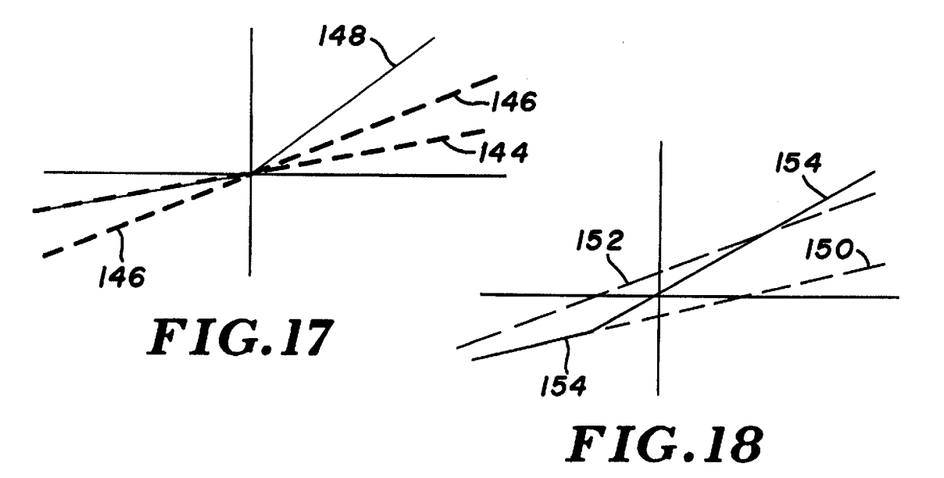
FIGS. 17–19 are charts illustrating restoring force as a function of axial elongation for different stent configurations.

Within the context of the different approaches to coupling the control members as discussed above, there are a variety of configurations that determine the nature of control member/latticework interaction. According to one stent configuration, the axial control member and the interbraided structural filaments are in the relaxed state simultaneously. This configuration is represented in FIG. 17, a plot of the restoring force due to the structural strands, and the restoring force due to the axial control member as a function of stent axial elongation. The vertical axis represents restoring force, and the horizontal axis represents axial elongation. At the intersection of the axes, the restoring force is zero, and the stent length and radius are at the nominal or relaxed-state values.

The inclined, broken line 144 plots the restoring force due to the structural strands alone. A broken line 146 similarly plots the restoring force due to the control member alone. A solid line 148 is the resultant restoring force of the structural strands and control member combined. To the left of the vertical axis, the resultant force and structural strand force coincide, indicating a slack control member that contributes no restoring force. To the right of this axis, the resultant restoring force represents the combined effect of increased tension in the control member and increased bending stress in the coiled structural strands as the coil radii become smaller.

The chart in FIG. 18 represents a stent with balanced, non-zero restoring forces in the nominal state. More particularly, an axial control strand is in tension, exerting a restoring force tending to axially shorten the stent. At the same time the helical structural strands exert a radial force, due to bending, tending to radially reduce/axially elongate the stent. Linear plots of the force of the structural strands and the force of the control strand are shown at 150 and 152, respectively. The resultant force is indicated by a solid line 154. Again, a coincidence of the resultant line and the structural strand force line indicates slack in the control strand, beginning at a pre-determined axial length less than the nominal length.

Figure 19:
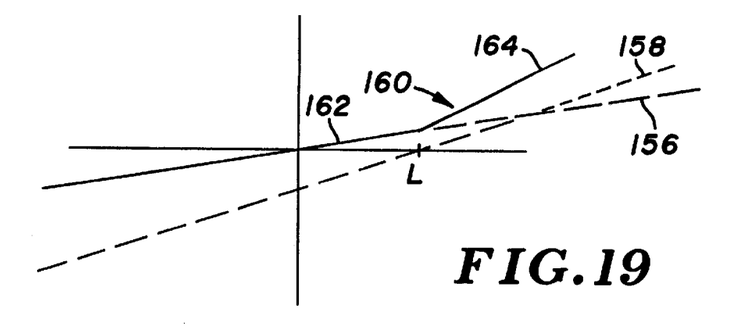

The chart in FIG. 19 represents a stent configuration in which the nominal, relaxed state is controlled solely by the structural strands, because of slack in the axial control strand. The structural strand force and control strand force are represented separately at 156 and 158, and their combined effect is shown by a solid line 160.

According to this configuration, there is an initial range of radial compression from the nominal size, represented by a segment 162 of line 160 having the more gentle slope, over which only the structural strands resist radial compression/axial elongation. Beyond a predetermined length L, however, radial compression is resisted by the structural strands and control member combined, for a considerably steeper slope along a segment 164.

A salient advantage of this configuration is that a stent can be designed to exert a gentle pressure against the surrounding tissue in a vessel slightly smaller than the nominal radius, yet also can exert considerably increased resistance when a muscular contraction or other event threatens to severely constrict the vessel.

In connection with FIGS. 17–19, the respective plots of control member restoring force can represent a combined force of several control members acting in concert. Further, if the control members involved were instead the larger-diameter type with substantial axial rigidity as shown in FIG. 7, the plots of structural strand force and resultant force would not coincide at larger radii as shown. Rather, at such radii the control members, under compression, would tend to resist further radial enlargement.

Thus, in accordance with the present invention, axial control members are coupled to tubular self-expanding prostheses to control the degree and nature of their radial expansion. Control members of substantially inextensible materials or recovery metals can be used to set definite limits on radial expansion. Alternatively, more resilient control members are used to augment the restoring force provided by the helically wound structural strands of the stent. The coupling of control strands at intermediate locations along the stent facilitates selective radial expansions to accommodate body lumen irregularities.

Each of the references cited in the foregoing specification is incorporated in its entirety, and for all purposes.

What is claimed is:

1. A body insertable prosthesis, including:

a body compatible prosthesis structure in the form of a braided tube having opposite open selvaged ends and comprising at least two oppositely directed sets of helically wound strands forming multiple intersections of oppositely directed pairs of strands, said braided tube further being enlargeable radially in concert with an axial shortening thereof, and alternatively reducible radially in concert with an axial elongation thereof; and at least one elongate control member coupled to the prosthesis structure at a first coupling location and further coupled to the prosthesis structure at a second coupling location spaced apart axially from the first coupling location in a manner that allows the control member to travel axially relative to the prosthesis structure while remaining substantially axially fixed relative to the prosthesis structure at the first coupling location, whereby an axial spacing between the first and second coupling locations is adjustable toward a selected spacing amount corresponding to a selected radius profile over a region of the prosthesis structure between the coupling locations, and wherein the first and second coupling locations are located at respective first and second ones of said intersections.

2. The prosthesis of claim 1 wherein:

the control member is slideably coupled to the prosthesis structure at the second coupling location.

3. The prosthesis of claim 2 further including:

a connector fixed to the prosthesis structure and adapted to receive the control member for sliding movement therein.

4. The prosthesis of claim 3 wherein:

the connector further is adapted to secure the control member integrally relative to the prosthesis structure at the second coupling location.

5. The prosthesis of claim 1 wherein:

the control member is fixed with respect to the prosthesis at the first coupling location, and the second coupling location further is coupled to allow a fixation thereof to set the axial spacing at said selected amount.

6. The prosthesis of claim 1 wherein:

the control member comprises a linear, axially extending strand.

7. The prosthesis of claim 6 wherein:

the strand is resilient.

8. The prosthesis of claim 7 wherein:

the prosthesis structure is resilient.

9. The prosthesis of claim 1 wherein:

at least one of the first and second coupling locations is disposed along a medial region of the prosthesis structure.

10. The prosthesis of claim 9 wherein:

the second coupling location is disposed along said medial region.

11. The prosthesis of claim 1 wherein:

the control member is thermally bonded to the prosthesis structure at the first location.

12. The prosthesis of claim 1 further including:

the plurality of the connectors mounted integrally to the strands at at least one of said open ends, to selvage the at least one open end.

13. The prosthesis of claim 12 wherein:

at least one of the connectors slideably receives the at least one control member.

14. The prosthesis of claim 13 wherein:

the prosthesis structure is resilient, and the at least one connector further is adapted to fixedly secure the at least one control member in a self-locking manner.

15. The prosthesis of claim 1 wherein:

the at least one control member comprises a plurality of substantially linear, axially extending strands, each strand having a first end fixed to the structure at the first coupling location.

16. The prosthesis of claim 15 wherein:

the first coupling location extends circumferentially about the prosthesis structure, and the associated first ends of the strands are circumferentially spaced apart from one another.

17. The prosthesis of claim 16 wherein:

each of the strands further is slideably coupled to the prosthesis at the second coupling location, and the second coupling location extends circumferentially about the structure.

18. The prosthesis of claim 1 wherein:

the control member is sufficiently rigid in the axial direction to push the prosthesis structure at the first coupling location, to axially elongate and radially reduce the prosthesis structure over said region between the coupling locations.

19. A braided prosthesis structure including:

a plurality of structural strands, intermingled with one another to form a generally tubular prosthesis structure enlargeable radially in concert with an axial shortening thereof and alternatively reducible radially in concert with an axial elongation thereof, the structure having two opposite open ends;

a plurality of connectors secured integrally to the strands at at least one of the open ends, to selvage at least one open end; and at least one elongate control strand fixed to the prosthesis structure at a fixation point and slideably received within an associated one of the connectors, whereby an axial spacing between the associated connector and the fixation point is adjustable by movement of the prosthesis structure relative to the control strand, thus to selectively adjust a radius profile of the structure over a region between the fixation point and the associated connector.

20. The prosthesis of claim 19 wherein:

the structural strands are arranged in at least two oppositely directed sets to form intersections of oppositely directed strands, and each of the connectors is joined to two oppositely directed ones of the strands.

21. The prosthesis of claim 20 wherein:

the associated connector further is adapted to secure the control strand in a fixed axial position relative to the associated connector.

22. A body insertable and controllably expandable prosthesis, including:

a body compatible, generally tubular prosthesis structure formed of a material lacking any substantial shape memory property, said prosthesis structure enlargeable radially in concert with an axial shortening thereof, and alternatively reducible radially in concert with an axial elongation thereof; and at least one control member constructed of a recovery metal, having a nominal shape defining a nominal length between first and second opposite ends thereof, plastically deformable to an altered shape defining an altered length between the opposite ends different than the nominal length, and tending to return to the nominal shape from the altered shape responsive to a predetermined change in temperature;

wherein the at least one control member, proximate said first and second ends, is joined integrally with respective first and second axially spaced apart locations along the prosthesis structure, whereby subjecting the plastically deformed control member to said predetermined temperature change alters an axial distance between the first and second locations, thus selectively adjusting a radius profile of the prosthesis structure along a region thereof between the first and second locations.

23. The prosthesis of claim 22 wherein:

the at least one control member has a substantially sinusoidal nominal shape and a linear altered shape when plastically deformed, whereby subjecting the control member to the predetermined temperature change axially shortens the structure along said region.

24. The prosthesis of claim 23 wherein:

the temperature change comprises an increase in temperature at least to a threshold level at which at least one control member tends to assume the nominal shape.

25. The prosthesis of claim 22 wherein:

the prosthesis structure is a braided tube comprising at least two sets of oppositely directed helically wound structural strands.

26. The prosthesis of claim 25 further including:

means for selvaging opposite open ends of the braided tube.

27. The prosthesis of claim 22 wherein:
said first and second locations are proximate opposite open ends of the prosthesis structure.

28. A body insertable prosthesis, including:
a body compatible and generally tubular prosthesis structure enlargeable radially in concert with an axial shortening thereof, and alternatively reduceable radially in concert with an axial elongation thereof; and
a plurality of substantially linear, axially extending strands, each strand having a first end fixed to the prosthesis structure at a first coupling location, each strand further coupled to the prosthesis structure at a second coupling location spaced apart axially from the first coupling location in a manner that allows the strand to travel axially relative to the prosthesis structure, whereby an axial spacing between the first and second coupling locations is adjustable toward a selected amount corresponding to a selected radius profile over a region of the prosthesis structure between the coupling locations.

29. The prosthesis of claim 28, wherein:
the first coupling location extends circumferentially about the prosthesis structure, and the associated first ends of the strands are circumferentially spaced apart from one another.

30. The prosthesis of claim 29, wherein:
each of the strands further is slideably coupled to the prosthesis structure at the second coupling location, and the second coupling location extends circumferentially about the structure.

31. The prosthesis of claim 28, wherein:
the prosthesis structure is a braided tube comprising at least two oppositely directed sets of helically wound strands forming multiple intersections of oppositely directed pairs of strands, and the first and second coupling locations are located at respective the first and second ones of said intersections.

32. A body insertable prosthesis, including:
a body compatible and generally tubular prosthesis structure enlargeable radially in concert with an axial shortening thereof, and alternatively reduceable radially in concert with an axial elongation thereof;
at least one elongate control member coupled to the prosthesis structure at a first coupling location in a manner to substantially fix the elongate control member axially relative to the prosthesis structure;
wherein the elongate control member further is coupled to the prosthesis structure at a second coupling location spaced apart axially from the first coupling location, in a manner that allows movement of the control member axially relative to the prosthesis structure to selectively vary an axial spacing between the first and second coupling locations toward a selected spacing amount and thereby selectively vary a radius profile, over a region of the prosthesis structure between the coupling locations toward a selected radius profile; and
wherein the control member and the prosthesis structure further are adapted to allow a fixation of the control member axially relative to the prosthesis structure at the second location after so selectively varying the axial spacing, to set the axial spacing at said selected spacing amount and thereby prevent any substantial radial reduction of the prosthesis structure over said region.

33. The prosthesis of claim 32, further including:
a connector fixed to the prosthesis structure at the second location and adapted to receive the control member for sliding movement therein.

34. The prosthesis of claim 33, wherein:
the connector further is adapted to secure the control member integrally relative to the prosthesis structure.

35. The prosthesis of claim 34, wherein:
the connector further is adapted to secure the control member in a self-locking manner.

36. The prosthesis of claim 32, wherein:
the control member is fixed with respect to the prosthesis structure at the first coupling location.

37. The prosthesis structure of claim 36, wherein:
the prosthesis structure is resilient, and the control member, when so fixed to set the axial spacing at the selected spacing amount, counteracts an elastic restoring force in the prosthesis structure to maintain the selected radius profile.

38. The prosthesis structure of claim 32, wherein:
the prosthesis structure is a braided tube comprising at least two oppositely directed sets of helically wound strands forming multiple intersections of oppositely directed pairs of strands, and the first and second coupling locations are located at respective the first and second ones of said intersections.

39. A body insertable prosthesis, including:
a body compatible and generally tubular prosthesis structure enlargeable radially in concert with an axial shortening thereof, and alternatively reduceable radially in concert with an axial elongation thereof;
at least one elongate control member coupled to the prosthesis structure at a first coupling location in a manner to substantially fix the elongate control member axially relative to the prosthesis structure;
wherein the elongate control member further is coupled to the prosthesis structure at a second coupling location spaced apart axially from the first coupling location, in a manner that allows axial movement of the control member relative to the prosthesis structure, to selectively vary an axial spacing between the first and second coupling locations toward a selected spacing amount, thereby to selectively vary a radius profile of the prosthesis structure, at least over a region thereof between the coupling locations, toward a selected radius profile corresponding to the selected spacing amount.

40. The prosthesis of claim 39, wherein:
said at least one elongate control member extends axially along the prosthesis structure.

41. The prosthesis of claim 39, wherein:
said control member and the prosthesis structure further are adapted to allow a fixation of the control member axially relative to the prosthesis structure at the second location after the axial spacing has been so selectively varied, to set the axial spacing at the selected spacing amount and thereby prevent any substantial radial reduction of the prosthesis structure over said region.

42. The prosthesis of claim 39, wherein:
the prosthesis structure is a braided tube comprising at least two oppositely directed sets of helically wound strands forming multiple intersections of oppositely directed pairs of strands, and the first and second coupling locations are located at respective the first and second ones of said intersections.

* * * * *